US005573654A

United States Patent [19]
Cheburkov et al.

[11] Patent Number: 5,573,654
[45] Date of Patent: Nov. 12, 1996

[54] PROCESS FOR MAKING HEXAFLUOROPROPANE AND PERFLUOROPROPANE

[75] Inventors: Yuri Cheburkov, Woodbury; John C. Hansen, Lakeland, both of Minn.

[73] Assignee: Minnesota Mining and Manufacturing Company, Saint Paul, Minn.

[21] Appl. No.: 205,636

[22] Filed: Mar. 4, 1994

[51] Int. Cl.$^6$ .............................. C25B 3/08; C07C 19/08; C07C 21/18
[52] U.S. Cl. .............................. 205/430; 570/142
[58] Field of Search .............................. 204/59 R, 59 F, 204/72, 81; 570/141, 142, 123

[56] References Cited

U.S. PATENT DOCUMENTS

| | | | |
|---|---|---|---|
| 983,009 | 6/1879 | Treat | 260/652 P |
| 2,519,983 | 8/1950 | Simons | 204/62 |
| 3,840,445 | 10/1974 | Paul et al. | 205/345 |
| 3,950,235 | 4/1976 | Benninger | 204/59 F |
| 3,962,348 | 6/1976 | Benninger et al. | 260/615 F |
| 5,068,473 | 11/1991 | Kellner et al. | 570/176 |
| 5,124,053 | 6/1992 | Iikubo et al. | 252/8 |
| 5,159,105 | 10/1992 | Hansen et al. | 560/125 |
| 5,171,901 | 12/1992 | Gassen et al. | 570/168 |
| 5,466,879 | 11/1995 | Cheburkov | 564/253 |
| 5,474,657 | 12/1995 | Hansen | 205/430 |

FOREIGN PATENT DOCUMENTS

| | | |
|---|---|---|
| 405615 | 1/1991 | European Pat. Off. . |
| 582192 | 2/1994 | European Pat. Off. . |
| 522639 | 1/1995 | European Pat. Off. . |
| 200980 | 6/1983 | German Dem. Rep. . |
| 53073504 | 6/1978 | Japan . |
| 55057526 | 4/1980 | Japan . |
| 6077983 | 5/1985 | Japan . |
| 63035539 | 2/1988 | Japan . |
| 2272086 | 11/1990 | Japan . |
| 130895 | 8/1960 | U.S.S.R. . |
| 423787 | 9/1974 | U.S.S.R. . |
| 879057 | 10/1961 | United Kingdom . |
| WO90/08748 | 8/1990 | WIPO . |

OTHER PUBLICATIONS

Drakesmith, F. G., et al., "Electrochemical Fluorination Using Porous Nickel and Foam Nickel Anodes," *J. of Fluorine Chem.*, vol. 32 (1986), pp. 103–134 no month.
Simons, J. H., et al., "The Electrochemical Process for the Production of Fluorocarbons," *J. of The Electrochemical Society*, vol. 95, No. 2, (1949), pp. 47–67 Feb.
Knunyants, *Synthesis of Fluoroorganic Compounds*, Springer-Verlag, Berlin, 1985, pp. 8, 9, and 103 (no month).
Van Der Puy, *J. of Fluorine Chem.*, 1979, pp. 375–378 (no month).
Dmowski, "Reactions of Sulfur Tetrafluoride With Carboxylic Acids. Part IV Reactions With Alkane–Dicarboxylic Acids," *Polish J. of Chem.*, 1978, pp. 71–85 (no month).
Aktaev, *Izv. Acad. Nauk. SSSR*, Ser. Khim., May 1977, pp. 1112–1117.
Drakesmith and Hughes, "The Electrochemical Fluorination of Propene," *J. of Appl. Electrochem.*, 1976, pp. 23–32 (no month).
Kocharyan et al., "Alkylating Properties of Alkyl Perfluoroisobutenyl Ethers," *Izv. Acad. Nauk. SSSR*, Ser. Khim., Apr. 1968, pp. 846–854.
Kocharyan et al., "Reactions of 2–Monohydroperfluoroisobutane and α–Hydrohexafluoroisobutyric Esters With Water in the Presence of Triethylamine," *Izv. Acad. Nauk. SSSR*, Ser. Khim., Aug. 1967, pp. 1847–1849.
Knunyants et al., "Perfluorodimethylketene and Perfluoromethacrylic Acid," *Izv. Acad. Nauk. SSSR*, Ser. Khim., Aug. 1963, pp. 1393–1397.
Cherburkov et al., "Bistrifluromethylketene and Perfluoromethacrylic Acid," *Izv. Acad. Nauk. SSSR*, Ser. Khim., Sep. 1963, pp. 1573–1576.
Hasek et al., "The Chemistry of Sulfur Tetrafluoride. II. The Fluorination of Organic Carbonyl Compounds," *J. Am. Chem. Soc.*, Feb. 1960, pp. 543–551.
Koshar et al., "The Addition of Alchohols to Octafluoroisobutene," *J. Am. Chem. Soc.* Apr. 1957, pp. 1741–1744.
Knunyants et al., "Reactions to Fluoro Olefins," *Izv. Acad. Nauk. SSR, Ser. Khim:* Nov. 1955, pp. 1387–1395 (Eng.).
Kocharyan et al., "Alkylating Properties of Alkyl Perfluoro–Isobuteryl Ethers", *Izv. Acad. Nauk. USSR*, Ser. Khim., 1968 (Apr.), pp. 846–854.
Khunyants et al., "Reactions of Fluoro Olefins", *Izv. Acad. Nauk. USSR*, Ser Khim., 1955 (Nov.), pp. 1387–1395.

Primary Examiner—Kathryn Gorgos
Assistant Examiner—Edna Wong
Attorney, Agent, or Firm—Douglas B. Little; Gary L. Griswold; Walter N. Kirn

[57] ABSTRACT

Perfluoroisobutene-MeOH adduct (2H-octafluororisobutyl methyl ether) is converted to hexafluoropropane by reaction with trialkyl amine (eg. triethyl amine) and $H_2O$. 1,1,1,3,3-Pentafluoropropene is also produced in lesser amounts. The electrolysis of the reaction product in anhydrous HF (at 10°–50° C., 0–140 kPa, and 50–300 amps/m$^2$ anode area) yields $C_3F_8$ and some $CF_3CFHCF_3$ which is condensed out of a gas stream from the electrolysis cell.

12 Claims, No Drawings

PROCESS FOR MAKING HEXAFLUOROPROPANE AND PERFLUOROPROPANE

TECHNICAL FIELD

This invention is in the field of fluorochemistry and fluorinated organic chemicals. More specifically, it pertains to synthesis of partially fluorinated and fully fluorinated propane.

BACKGROUND

In response to environmental concerns, the use of chlorofluorocarbons (CFCs) and their production is being phased out. Industry is currently seeking chlorine-free alternatives that have a very low ozone depletion potential (ODP) and have little or no contribution to global warming (GWP or global warming potential).

One compound, having short atmospheric lifetime, lower GWP and very low ODP is 1,1,1,3,3,3-hexafluoropropane, also referred to as HFC-236fa, which has been suggested as a fire extinguishing composition, propellant, blowing agent in the manufacture of polymer foams, heat exchange fluid or refrigerant and solvent for cleaning, degreasing and defluxing of electronic devices. Heptafluoropropane, also called HFC-227ea, has been suggested as a fire extinguishing agent. Perfluoropropane has been used as a dielectric gas, heat transfer medium, blowing agent in the production of polyolefin foams, and dry etching material in the manufacture of semiconductors.

Hexafluoropropane has been prepared by a number of methods including: electrochemical fluorination of propene; catalytic hydrofluorination of hexachloropropane or hexachloropropene; and fluorination of malonic acid with either sulfur tetrafluoride or molybdenum hexafluoride. Knunyants, et al. has described a preparation from decarboxylation of the 2H-hexafluoroisobutyric acid and the corresponding potassium salt, and from hydrolyses of both the 2H-hexafluoroisobutyryl fluoride/triethylamine and heptafluoroisobutenyl methyl ether/triethylamine complexes. (See Knunyants et al., Izv. Akad. Nauk. Ser. Khim., Eng. Ed., 1963., pp. 1269–1272; Cheburkov et al., Ibid., 1963, pp. 1435–1438; and Kocharyan, et al., Ibid., 1968, pp. 810–816).

Perfluoroisobutene, ("PFIB" or $(CF_3)_2C=CF_2$) is a byproduct in the manufacture of hexafluoropropene. It is a highly toxic, colorless gas which may be converted to the less harmful methanol adduct and destroyed. U.S. Defensive Publication T983,009 (Treat) describes a process for converting PFIB into the methanol adduct. Other processes for converting PFIB to less harmful materials are described in Chemical Abstracts (C.A.)99(24):199919d (East German patent publication DD 200,0(7):54449e (Japanese Kokai 78 73,504).

The process of electrolyzing liquid hydrogen fluoride (HF) containing an organic chemical which can be fluorinated, at an electrical potential insufficient to generate free fluorine but sufficient to cause fluorination of the organic chemical (known as the Simons process, electrochemical fluorination, or ECF) is old in the art (see U.S. Pat. No. 2,519,983).

DISCLOSURE OF INVENTION

A process has been invented which can be used to convert PFIB-alkanol adduct into hexafluoropropane, and further to convert hexafluoropropane into perfluoropropane by ECF.

The inventive process is summarized as a process for making hexafluoropropane comprising reacting a compound selected from the group consisting of 2H-octafluoroisobutyl alkyl ethers, heptafluoroisobutenyl alkyl ethers and mixtures thereof with a trialkyl amine and water to yield hexafluoropropane.

It is a short reaction route in which PFIB-alkanol adduct (such as 2H-octafluoroisobutyl methyl ether and heptafluoroisobutenyl methyl ether) may be reacted directly with a trialkylamine (such as triethylamine) or pyridine and water to yield hexafluoropropane. The heptafluoroisobutenyl alkyl ether in the reaction mentioned above can be obtained by dehydrofluorinating the 2H-octafluoroisobutyl alkyl ether.

In the experimental work of developing this process of preparing hexafluoropropane, the reaction product has been found to contain a certain proportion (e.g., about 10%) of 1,1,1,3,3-pentafluoropropene. Another reaction product is a water solution of methyltriethylammonium hydrobifluoride, which may be useful in the same way as many tetraalkylammonium salts.

The invention further comprises making perfluoropropane by:

A. placing in an electrolysis apparatus (or cell) a current-conducting liquid mixture containing anhydrous hydrogen fluoride and the hexafluoropropane (and alternatively, or in addition, pentafluoropropene); and B. Electrolyzing the mixture at a temperature and pressure sufficient to maintain liquid state in the apparatus and at a voltage insufficient to generate free fluorine but which is sufficient to cause fluorination of the hexafluoropropane (and, if present, pentafluoropropene) to perfluoropropane.

This represents an improved route to perfluoropropane, because the starting material for the ECF ( $(CF_3)_2CH_2$) is already partially fluorinated. The electrolysis cell may be more efficiently utilized than if it were to make the same product from another raw material, such as propane.

DETAILED DESCRIPTION

PFIB methanol adduct can comprise 2H-octafluoroisobutyl methyl ether, $(CF_3)_2CHCF_2OCH_3$ and heptafluoroisobutenyl methyl ether,$(CF_3)_2C=CFOCH_3$. The adduct mixture can be distilled to produce a composition which is predominantly the saturated or the unsaturated ether; although, this is not necessary to prepare hexafluoropropane.

The inventive process can be illustrated by the reaction sequence from PFIB and methanol to hexafluoropropane given below. In this sequence, the trialkyl amine is triethylamine, but other trialkyl amines (having 1–4 carbon atoms in the alkyl groups) may be used. Similarly, any alcohol which will react with PFIB to produce an alcohol adduct may be used. Lower primary alcohols such as methanol, ethanol and propanol are preferred due to their ready reactivity with PFIB, their cost and availability.

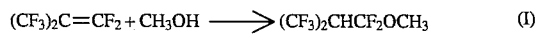

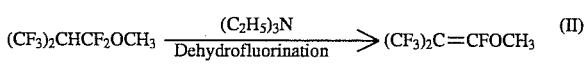

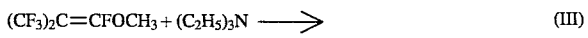

-continued

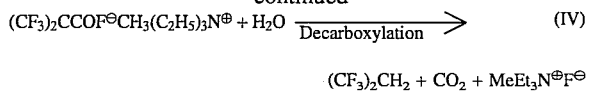

$$(CF_3)_2CH_2 + CO_2 + MeEt_3N^{\oplus}F^{\ominus}$$

Reactions II–IV can occur at the same time. The reaction conditions may be: temperature in the range 0°–40° C.; pressure range of atmospheric pressure to 690 kPa; and reaction time of 0.5 to 1 hour.

Although any addition order may work, the water is preferably added slowly to the cold mixture of 2H-octafluoroisobutyl methyl ether and trialkylamine, after the trialkyl amine has been added, because, if the water is added first, the evolution of $CO_2$ may be violent.

According to the reaction equation, two moles of triethylamine are needed to accomplish the process. It has been found that one mole of the tertiary amine is enough to obtain a good yield of hexafluoropropane. The second hydrogen fluoride molecule is retained by the tetraalkylammonium fluoride as an acidic salt $MeEt_3N^{\oplus}HF_2^{\ominus}$.

The gases evolved during the reaction (containing hexafluoropropane and pentafluoropropene) are captured in a cold trap connected to the reactor. Then, they can be purified by recondensation (essentially a bulb-to-bulb distillation) or distillation.

The inventive synthesis of hexafluoropropane will be further illustrated by following examples:

EXAMPLE 1

Hexafluoropropane from PFIB-Methanol adduct

A mixture of 2H-octafluoroisobutyl methyl ether $(CF_3)_2CHCF_2OCH_3$ (17.5 g, 75 mmol) and triethylamine (7.75 g, 77 mmol) was stirred at room temperature for 2 hours until it became homogenous. Water (3.0 g, 167 mmol) was slowly added dropwise and the resulting volatile product was collected in a cold trap maintained at −78° C. Upon complete addition of the water, the mixture was heated to 55° C. with a nitrogen purge. The product (9.94 g) consisted of: 84% hexafluoropropane, 8% pentafluoropropene and 8% starting material as shown by gas chromatography. The product was further purified by recondensation of the low boiling fraction to lower the starting material content to approximately 2%. The residue in the reactor (14.2 g) was a slightly yellow water solution of methyltriethylammonium hydrobifluoride. The yields (based on the starting material consumed) were: hexafluoropropane 77% and pentafluoropropene 8%. The structure and purity of all products was confirmed by gas chromatograph (GC), mass spectrometer (MS) analysis, and by $^1H$ and $^{19}NMR$.

EXAMPLE 2

Hexafluoropropane from PFIB-Methanol adduct using an excess of triethylamine.

Using essentially the same procedure described in Example 1 a mixture of 17.7 g (77mmol) 2H-octafluoroisobutyl methyl ether, 10.3 g (102 mmol) triethylamine was left at 20° C. overnight. The mixture was not completely homogeneous, and the upper layer was almost pure triethylamine. Water 3 g (167 mmol) was added dropwise and 11.73 g of volatile products were collected in the cold trap as before. GC analysis of the product revealed 81% hexafluoropropane, 13% pentafluoropropene and 5% starting octafluoroisobutyl methyl ether. The yields based on the starting material consumed were: hexafluoropropane 85% and pentafluoropropene 15% as determined by GC.

When a ratio of 2 moles of triethylamine to 1 mole of the ether was used, the low boiling mixture in the cold trap did not contain the starting ether. More than 99% of the mixture collected comprised the hexafluoropropane and pentafluoropropene, with an overall yield of 86%. Excess triethylamine was recovered from the residue by distillation under a slight vacuum.

EXAMPLE 3

Hexafluoropropane from heptafluoroisobutenyl methyl ether.

Heptafluoroisobutenyl methyl ether, was prepared by treatment of 2H-octafluoroisobutyl methyl ether with 50% aqueous potassium hydroxide followed by distillation. Triethylamine (5.20 g, 0.05M) was added gradually to a stirred mixture of 10.41 g (0.05M) heptafluoroisobutenyl methyl ether (94% purity with 1.5% of 2H-octafluoroisobutyl methyl ether and 4% of methyl-2H-hexafluoroisobutyrate) and 5 ml of water maintained at 10° C. Upon complete addition of the triethylamine the reaction mixture was refluxed and volatile products collected in the cold trap as previously described. Starting material (0.65 grams, 96% purity) was collected from the reaction vessel by washing the contents with 10% sulfuric acid followed by water. The contents of the cold trap were recondensed as described in Example 1 to yield 4.83 g of a mixture of hexafluoropropane (90%), pentafluoropropene (8%), 2H-octafluoroisobutyl methyl ether (2%) as determined by GC analysis. A residue (0.75 g) from the recondensation was a mixture of hexafluoropropane (16%) and 2H-octafluoroisobutyl methyl ether (78%). The yield of the hexafluoropropane-pentafluoropropene mixture was 71% based on starting material.

EXAMPLE 4

Hexafluoropropane from PFIB-Ethanol adduct. PFIB was generated by pyrolysis of hexafluoropropene using the procedure described in "Synthesis of Fluoroorganic Compounds" I. L. Knunyants and Jacobson, eds., Springer-Verlag, Berlin, Heidelberg, New York, Tokyo, 1985, p. 8. The PFIB thus generated was immediately quenched by bubbling through ethanol to produce the PFIB-ethanol adduct. The adduct was isolated by washing with water followed by distillation, boiling point 89°–89° C.

GC analysis of this starting material revealed it to be a mixture of 89% 2H-octafluoroisobutyl ethyl ether and 10% heptafluoroisobutenyl ethyl ether. Using the procedure of Example 1 8.77 g (0.036M) of the starting material and 6.75 g (0.067M) of triethylamine were stirred at 20° C., followed by treatment with water. The volatile products were isolated as before to yield 4.3 g of crude mixture containing 85.5% hexafluoropropane, 4.5% pentafluoropropene, and 7.8% 2H-octafluoroisobutyl ethyl ether, as determine by GC. After recondensation in another trap the starting ether content was lowered to 1%. The yield of the propanepropene mixture was 71%.

This process allows the efficient utilization of byproducts of industrial hexafluoropropene production: either 2H-octafluoroisobutyl alkyl ethers or heptafluoroisobutenyl alkyl ethers or their mixtures, resulting in high yield (>80%) of 1,1,1,3,3,3-hexafluoropropane and 1,1,1,3,3-pentafluoropropene and potentially useful co-product methyltriethylammonium fluoride, using moderate reaction conditions and available reagents.

Electrochemical Fluorination

The hexafluoropropane and pentafluoropropene can be further fluorinated in an ECF cell. ECF cells typically contain a suspended monopolar electrode assembly, i.e., electrodes (closely spaced, alternating iron cathode plates and nickel anode plates) connected in parallel through electrode posts to a source of direct current at relatively low voltage (e.g., 4–9 volts). The cell body, typically made of carbon steel (which may have a coating of corrosion resistant material), usually has: a cooling jacket; an outlet pipe at the bottom through which can be drained the cell product; an inlet pipe at the top for charging the cell; and an outlet pipe at the top of the cell for removing gaseous cell products.

The gaseous stream leaving the reactor can comprise HF, Hydrogen, $OF_2$ (oxygen difluoride), and other gases. The top outlet pipe can be connected to a refrigerated condenser (cold trap), or a series of condensers, to condense HF vapors to be returned to the cell. The cold trap can be cooled with liquid nitrogen ($-196°$ C.) or dry ice (solid $CO_2$ at $-78°$ C.). The gas stream from the top of the cell may pass through a packed bed of catalyst (e.g., silver or silver fluoride on alumina support) in which $OF_2$ is removed. U.S. Pat. No. 2,519,983, which contains more details regarding ECF cells including a drawing, is incorporated herein by reference.

ECF cells vary in size from small cells, which run at currents of from less than one ampere to more than 100 amps, to large cells, which use 10,000 amps or more. Such cells can be run batch-wise, semicontinuously, or continuously, and at constant voltage or constant current. The level of liquid in the cell is preferably controlled, and both the HF and the organic chemical being fluorinated can be replenished from time to time.

In the inventive ECF process, the following conditions are useful:

weight percent HF in cell liquid—80 to 99, preferably 90 to 99%;

weight ratio HF to (hexafluoropropane and pentafluoropropene)—9:1 to 10:1;

typical ratio of hexafluoropropane to pentafluoropropene—19:1 to 5:1, typically 8:1;

temperature range—$-10°$ C. to 70° C., preferably less than 50° C., typically at boiling conditions for the liquid in the cell (boiling point of HF being about 20° C. at atmospheric pressure), but a liquid phase is maintained;

cell pressure—atmospheric pressure to 450 kiloPascals (kPa), typically below 250 kPa, preferably below 140 kPa;

average current density in the cell during electrolysis—40 to 800 amps per square meter (amps/m$^2$) of active anode surface area, typically 50 to 300 amps/m$^2$;

continuous mode of operation for 100 to 300 hours; ≦10 weight percent of a conductivity additive present in the HF electrolyte. Conductivity additives are known in the art and are for the purpose of increasing conductivity and also reducing the formation of high molecular weight polymer and tar during ECF. Some useful conductivity additives are thiols (such as methane thiol), dimethyldisulfide, methyl sulfide, and methyl acetate.

Temperature can be controlled by controlling back pressure in the cell itself, by means of a back pressure control valve on the gas outlet line.

EXAMPLE 5

An ECF cell of 180 cm$^3$ total electrolyte volume was operated in accordance with the general procedure described above. The organic liquid to be fluorinated in the cell (which was added batchwise to the cell) was an 8/1 weight ratio mixture of hexafluoropropane/pentafluoropropene plus small amounts of triethyamine. The ECF was operated at 69–140 kPa and 35°–450° C. Current density was about 226 amps/m$^2$ at operating conditions of 6.5 volts and 103 kPa. The condensing system was operated at $-40°$ C. The cell was operated for 71 hours. Yield of $C_3F_8$ was estimated at 61 grams/50amp-hr. Both perfluoropropane and heptafluoro-2-hydrido propane were produced. The ratio of $C_3F_8$ to $C_3F_7H$ (heptafluoro-2-hydridopropane) was about 10:1.

This ECF process provides a route to produce $C_3F_8$ which is a valuable material for use as a refrigerant, either alone or as a part of a mixture with other gases. This technique, using a partially fluorinated raw material, results in higher current yields per cell hour than does a total hydrocarbon raw material, such as propane. There is also less hydrogen evolved from the system, making condensation more efficient at any given collection temperature.

What is claimed is:

1. A process for making hexafluoropropane consisting essentially of reacting in a single step an ether compound selected from the group consisting of 2H-octafluoroisobutyl alkyl ethers with a trialklyl amine and water to yield hexafluoropropane, provided that in said process the ether compound, trialkyl amine and water are mixed together in a single vessel.

2. The process of claim 1 which is performed in the absence of a solvent for the reactants.

3. The process of claim 1 in which the reaction also produces 1,1,1,3,3-pentafluoropropene.

4. The process of claim 3 further comprising the production of perfluoropropane by:

A. making a current-conducting liquid mixture containing the 1,1,1,3,3-pentafluoropropene and hydrogen fluoride in an electrolysis cell containing an anode; and B. electrolyzing said liquid mixture under the following conditions: pressure in the range of about atmospheric pressure to 250 kPa; temperature to maintain a boiling liquid phase in the cell; average current density of about 50 to 300 amps per square meter of anode surface area; and a voltage insufficient to generate free fluorine but which causes fluorination of the 1,1,1,3,3-pentafluoropropene to perfluoropropane.

5. The process of claim 1 in which the trialkyl amine is triethyl amine.

6. The process of claim 1 in which the ether compound is selected from 2H-octafluoroisobutyl methyl ether, heptafluoroisobutenyl methyl ether, and mixtures thereof.

7. The process of claim 1 further comprising the production of perfluoropropane by:

A. making a current-conducting liquid mixture containing the hexafluoropropane and hydrodogen fluoride in an electrolytic cell containing an anode; and B. electrolyzing said liquid mixture under the following conditions: pressure in the range of about atmospheric pressure to 250 kPa; temperature to maintain a boiling liquid phase in the cell; average current density of about 50 to 300 amps per square meter of anode surface area; and a voltage insufficient to generate free fluorine but which causes fluorination of the hexafluoropropane to perfluoropropane.

8. The process of claim 1 in which one mole of trialkyl amine is used per mole of said ether compound.

9. The process of claim 1 in which the reaction takes place at a temperature in the range of 0°—40° C.

10. A process for making perfluoropropane comprising:

A. making a current-conducting liquid mixture of hexafluoropropane, 1,1,1,3,3-pentafluoropropene and hydrogen fluoride in an electrolysis cell containing an anode; and B. electrolyzing said liquid mixture under the following conditions: pressure in the range of about atmospheric pressure to 250 kPa; temperature to maintain a boiling liquid phase in the cell; average current density of about 50 to 300 amps per square meter of anode surface area; and a voltage insufficient to generate free fluorine but which is causes fluorination of the hexafluoropropane and 1,1,1,3,3-pentafluoropropene to perfluoropropane.

11. The process of claim 10 in which the weight ratio of hydrogen fluoride to the sum of the weights of hexafluoropropane and 1,1,1,3,3-pentafluoropropene is in the range of 9:1 to 10:1.

12. A process for making hexafluoropropane consisting essentially of reacting in a single step an ether compound selected from the group consisting of 2H-octafluoroisobutyl alkyl ethers, heptafluoroisobutenylalkyl ethers and mixtures thereof with a trialklyl amine and water to yield hexafluoropropane, provided that the ether compound, the trialkyl amine and the water are mixed together in a single vessel.

* * * * *

UNITED STATES PATENT AND TRADEMARK OFFICE
CERTIFICATE OF CORRECTION

PATENT NO.: 5,573,654
DATED: November 12, 1996
INVENTOR(S): Yuri Cheburkov and John C. Hansen It is certified that error appears in the above-identified patent and that said Letters Patent is hereby corrected as shown below:

Column 1, line 53
 "DD200,0(7)" should be -- DD 200,980): and C.A. 90(7) --

Column 3, line 20
 "N⊕HF$_2$⊖" should be -- N$^\oplus$HF$_2$$^\ominus$ --

Column 3, line 50
 "$^{19}$NMR" should be -- $^{19}$F NMR --

Column 6, line 5
 "450° C" should be -- 45° C --

Signed and Sealed this

Twenty-third Day of September, 1997

Attest:

BRUCE LEHMAN

Attesting Officer  Commissioner of Patents and Trademarks